(12) United States Patent
Glaser et al.

(10) Patent No.: US 8,211,403 B2
(45) Date of Patent: Jul. 3, 2012

(54) RADIOLABELLING METHODS

(75) Inventors: Matthias Eberhard Glaser, London (GB); Erik Arstad, London (GB)

(73) Assignee: Hammersmith Imanet Limited, London (GB)

( * ) Notice: Subject to any disclaimer, the term of this patent is extended or adjusted under 35 U.S.C. 154(b) by 666 days.

(21) Appl. No.: 12/305,253

(22) PCT Filed: Jun. 20, 2007

(86) PCT No.: PCT/GB2007/002303
§ 371 (c)(1),
(2), (4) Date: Jun. 16, 2009

(87) PCT Pub. No.: WO2007/148089
PCT Pub. Date: Dec. 27, 2007

(65) Prior Publication Data
US 2010/0040550 A1 Feb. 18, 2010

Related U.S. Application Data

(60) Provisional application No. 60/805,369, filed on Jun. 21, 2006.

(51) Int. Cl.
*A61K 51/00* (2006.01)
*A61M 36/14* (2006.01)

(52) U.S. Cl. ............ 424/1.69; 424/1.73; 424/1.81; 424/1.85; 424/1.89

(58) Field of Classification Search ............ 424/1.69, 424/1.73, 1.81, 1.85, 1.89; 530/300, 317, 530/329; 534/10–16
See application file for complete search history.

(56) References Cited

FOREIGN PATENT DOCUMENTS

| WO | 03/006491 | 1/2003 |
|---|---|---|
| WO | 03/101972 | 12/2003 |
| WO | 2004/055160 | 7/2004 |
| WO | 2006/017619 | 2/2006 |
| WO | 2006/067376 | 6/2006 |
| WO | 2006/116629 | 11/2006 |

OTHER PUBLICATIONS

Hansen, T.V. "One-pot copper(I)-catalyzed synthesis of 3,5-disubstituted isoxazoles" J. Org. Chem, vol. 71, Aug. 13, 2005 pp. 7761-7764.
Schoenbaechler, R. et.al. "Synthesis and 11C-radiolabelling of a tropane derivative lacking the 2 beta ester group: a potential pet-tracer for the dopamine transporter" Labelled CPD Radiopharm, vol. 42, 1999, pp. 447-456.
Link, A James, et.al. "Cell surface labeling of *Escherichia coli* via copper(I)-catalyzed (3+2) cycloaddition" Journal of the American Chemical Society, Washington, D.C. US, vol. 125, No. 37, Sep. 17, 2003 pp. 11164-11165.
Perez-Balderas, et.al. "synthesis of multivalent neoglycoconjugates by 1,3 dipolar cycloaddition of nitrile oxides and alkynes and evaluation of their lectin-binding affinities" Tetrahedron, Elsevier Science Publishers, Amsterdam, NL, vol. 61, No. 39, Sep. 26, 2005, pp. 9338-9348.
Cereda E., et.al. "Solid-phase synthesis of 3-hydroxymethyl isoxazoles via resin bound nitrile oxides" Tetrahedron Letters, Elsevier, Amsterdam, NL, vol. 42, No. 30, Jul. 23, 2001 pp. 4951-4953.
Hu, Y. et.al. "Quantitative predictions of substitutent and solvent effects on the regioselectivities of nitrile oxide cycloadditions to electron-deficient alkynes" Tetrahedron, Elsevier Science Publishers, Amsterdam, NL, vol. 56, No. 42, Oct. 13, 2000, pp. 8239-8243.
Giguere, D. et.al. "Carbohydrate triazoles and isoxazoles and inhibitors of galectins-1 and -3" Chem. Chommun., Mar. 16, 2006, pp. 2379-2381.
Huisgen, R, "1,3-dipolar cycloadditions past and future" Angewandte Chemie Int'l Edition, vol. 2, No. 10, Oct. 1963, pp. 565-632.
Sutcliffe-Goulden, J.L., et.al. "Rapid solid phase synthesis and biodistribution of 18F-labelled linear peptides" European Journal of Nuclear Medicine vol. 29, No. 6, Mar. 26, 2002 pp. 754-759.
Meyer, A.G. et.al. "Beta-cyclodextrin as a scaffold for supramolecular chemistry, to revers the regioselectivity of nitrile oxide cycloadditions" J. Org. Chem, vol. 63, Nov. 10, 1998, pp. 9069-9075.
Dondoni, A. et.al. "Assembling heterocycle-tethered C-glycosyl and alpha-amino acid residues via 1,3-dipolar cycloaddition reactions" Organic Letters, vol. 6, No. 17, Jul. 30, 2004 pp. 2929-2932.
Speers, A.E. et.al. "Activity-based protein profiling in vivo using a copper(I)-catalyzed azide-alkyne [3+2] cycloaddition" J. Am. Chem. Soc., vol. 125, Mar. 28, 2003, pp. 4686-4687.
Glaser, M. et.al. ""Click labeling" with 2-[18F]fluorethylazide for positron emission tomography" Bioconjugate Chem vol. 18, Apr. 14, 2007, pp. 989-993.

(Continued)

*Primary Examiner* — Michael G Hartley
*Assistant Examiner* — Jagadishwar Samala

(57) ABSTRACT

The invention relates to radiodiagnostic and radiotherapeutic agents, including biologically active vectors labelled with radionuclides. It further relates to methods and reagents labelling a vector such as a peptide comprising reaction of a compound of formula (I): with a compound of formula (II) or, a compound of formula (III): with a compound of formula (IV): in the presence of a Cu (I) catalyst. The resultant labelled conjugates are useful as diagnostic agents, for example, as radiopharmaceuticals more specifically for use in Positron Emission Tomography (PET) or Single Photon Emission Computed Tomography (SPECT) or for radiotherapy.

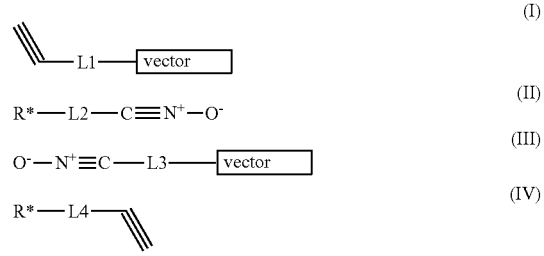

18 Claims, No Drawings

OTHER PUBLICATIONS

Marik, J. et.al. "Click for PET: rapid preparation of [18F]fluoropeptides using CuI catalyzed 1,3-dipolar cycloaddition" Tetrahedron Letters, vol. 47, Jul. 31, 2006, pp. 6681-6684.

Haka, et.al. "Aryltrimethylammonium trifluoromethanesulfonates as precursors to aryl [18F]fluorides: improved synthesis of [18F]GBR-13119" j. Labelled Compounds and Radiopharmaeuticals vol. 27, No. 7 Dec. 1988.

PCT/GB2007/002303 Int'l search report/written opinion dated Dec. 2007.

RADIOLABELLING METHODS

This application is a filing under 35 U.S.C. 371 of international application number PCT/GB2007/002303, filed Jun. 20, 2007, which claims priority to application No. 60/805,369 filed Jun. 21, 2006, in Great Britain the entire disclosure of which is hereby incorporated by reference.

The present invention relates to radiodiagnostic and radiotherapeutic agents, including biologically active vectors labelled with radionuclides. It further relates to methods and reagents labelling a vector such as a peptide. The resultant labelled conjugates are useful as diagnostic agents, for example, as radiopharmaceuticals more specifically for use in Positron Emission Tomography (PET) or Single Photon Emission Computed Tomography (SPECT) or for radiotherapy.

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases. Other useful radionuclides include $^{11}$C, radioiodine such as $^{125}$I, $^{123}$I, $^{124}$I, $^{131}$I and $^{99m}$Tc.

To date, a lack of rapid and generally applicable methods for peptide and biomolecule labelling has hampered the use of peptides and biomolecules as diagnostic agents. For example, almost all of the methodologies currently used today for the labelling of peptides and proteins with $^{18}$F utilize active esters of the fluorine labelled synthon. As peptides and proteins may contain a multitude of functional groups capable of reaction with active esters these current methods are not site-specific. For example a peptide containing three lysine residues has three amine functions all equally reactive towards the labelled synthon. Therefore, there still exists a need for labelling agents such as $^{18}$F-labelled prosthetic groups and methodologies, which allow rapid, chemoselective introduction of a label such as a radionuclide, for example $^{18}$F, particularly into peptides, under mild conditions to give labelled products in high radiochemical yield and purity. Additionally, there is a need for such methodologies which are amenable to automation to facilitate preparation of diagnostic agents in the clinical setting.

The present invention provides a method for labelling a vector comprising reaction of a compound of formula (I) with a compound of formula (II):

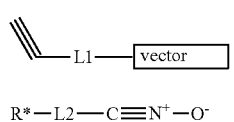

or, a compound of formula (III) with a compound of formula (IV)

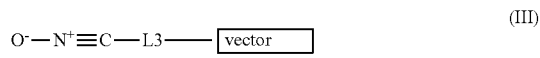

in the presence of a Cu (I) catalyst, wherein:
L1, L2, L3, and L4 are each Linker groups;
R* is a reporter moiety which comprises a radionuclide;
to give a conjugate of formula (V) or (VI) respectively:

wherein L1, L2, L3, L4, and R* are as defined above.

The Linker groups L1, L2, L3, and L4 are each independently a $C_{1-60}$ hydrocarbyl group, suitably a $C_{1-30}$ hydrocarbyl group, optionally including 1 to 30 heteroatoms, suitably 1 to 10 heteroatoms such as oxygen or nitrogen. Suitable Linker groups include alkyl, alkenyl, alkynyl chains, aromatic, polyaromatic, and heteroaromatic rings any of which may be optionally substituted for example with one or more ether, thiooether, sulphonamide, or amide functionality, monomers and polymers comprising ethyleneglycol, amino acid, or carbohydrate subunits.

The term "hydrocarbyl group" means an organic substituent consisting of carbon and hydrogen, such groups may include saturated, unsaturated, or aromatic portions.

The Linker groups L1, L2, L3, and L4 may be chosen to provide good in vivo pharmacokinetics, such as favourable excretion characteristics in the resultant compound of formula (V) or (VI). The use of linker groups with different lipophilicities and or charge can significantly change the in vivo pharmacokinetics of the peptide to suit the diagnostic need. For example, where it is desirable for a compound of formula (V) or (VI) to be cleared from the body by renal excretion, a hydrophilic tinker is used, and where it is desirable for clearance to be by hepatobiliary excretion a hydrophobic linker is used. Linkers including a polyethylene glycol moiety have been found to slow blood clearance which is desirable in some circumstances.

R* is a reporter moiety which comprises a radionuclide for example a positron-emitting radionuclide. Suitable positron-emitting radionuclides for this purpose include $^{11}$C, $^{18}$F, $^{75}$Br, $^{76}$Br, 124I, $^{82}$Rb, $^{68}$Ga, $^{64}$Cu and $^{62}$Cu, of which $^{11}$C and $^{18}$F are preferred. Other useful radionuclides include $^{123}$I, $^{125}$I, $^{131}$I, $^{211}$At, $^{99m}$Tc, and $^{111}$In. Metallic radionuclides are suitably incorporated into a chelating agent, for example by direct incorporation by methods known to the person skilled in the art. Chelation of a metallic reporter is preferably performed prior to reaction of the compound of formula (I) or (IV) with a compound of formula (II) or (III) respectively, to avoid chelation of the Cu(I) catalyst.

Suitable chelating agents comprised in R*, include those of Formula X

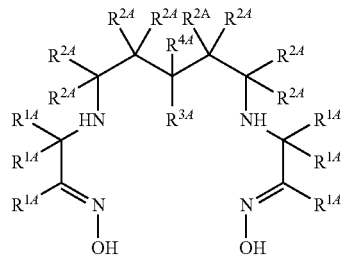

(X)

where:

each $R^{1A}$, $R^{2A}$, $R^{3A}$ and $R^{4A}$ is independently an $R^A$ group;

each $R^A$ group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more $R^A$ groups, together with the atoms to which they are attached form a carbocyclic, heterocyclic, saturated or unsaturated ring, or R* can comprise a chelating agent given by formula (i), (ii), (iii), or (iv)

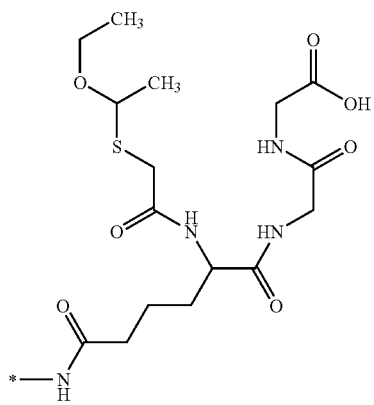

(i)

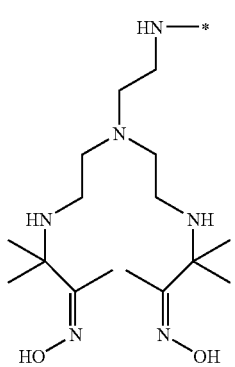

(ii)

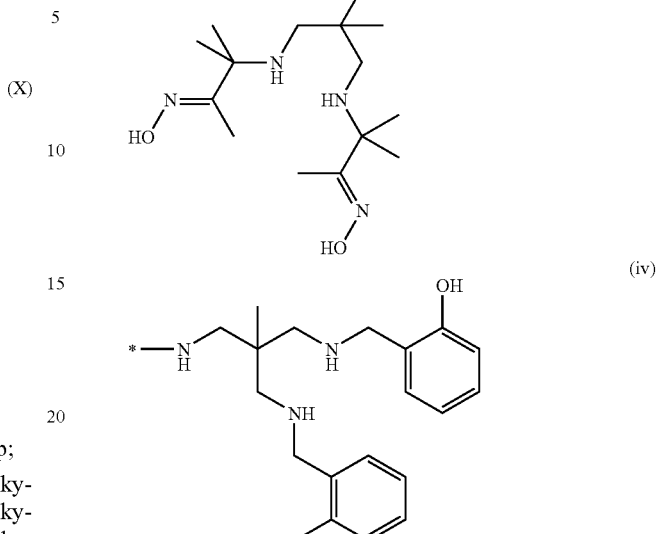

(iii)

(iv)

A preferred example of a chelating agent is represented by formula (v).

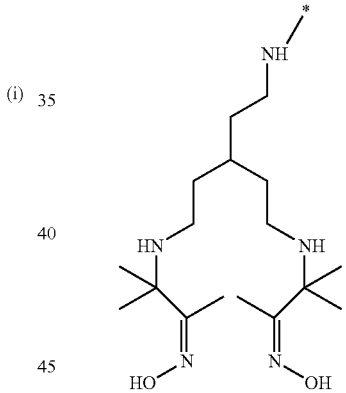

(v)

Compounds of formula (II) or (IV) comprising chelating agents of Formula X can be radiolabelled to give good radiochemical purity (RCP), at room temperature, under aqueous conditions at near neutral pH.

In formulae (I) and (III) and in other aspects of the invention unless specifically stated otherwise, suitable vectors for labelling are peptides, which may include somatostatin analogues, such as octreotide, bombesin, vasoactive intestinal peptide, chemotactic peptide analogues, α-melanocyte stimulating hormone, neurotensin, Arg-Gly-Asp peptide, human pro-insulin connecting peptide, insulin, endothelin, angiotensin, bradykinin, endostatin, angiostatin, glutathione, calcitonin, Magainin I and II, luteinizing hormone releasing hormone, gastrins, cholecystochinin, substance P, vasopressin, formyl-norleucyl-leucyl-phenylalanyl-norleucyl-tyrosyl-lysine, Annexin V analogues, Vasoactive Protein-1 (VAP-1) peptides, and caspase peptide substrates. Preferred peptides for labelling are Arg-Gly-Asp peptide and its analogues, such as those described in WO 01/77415 and WO 03/006491, preferably a peptide comprising the fragment

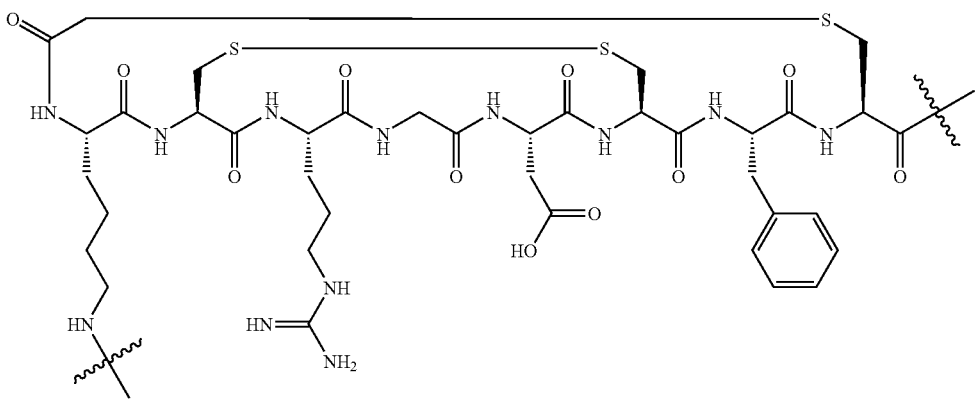

more preferably the peptide of formula (A):

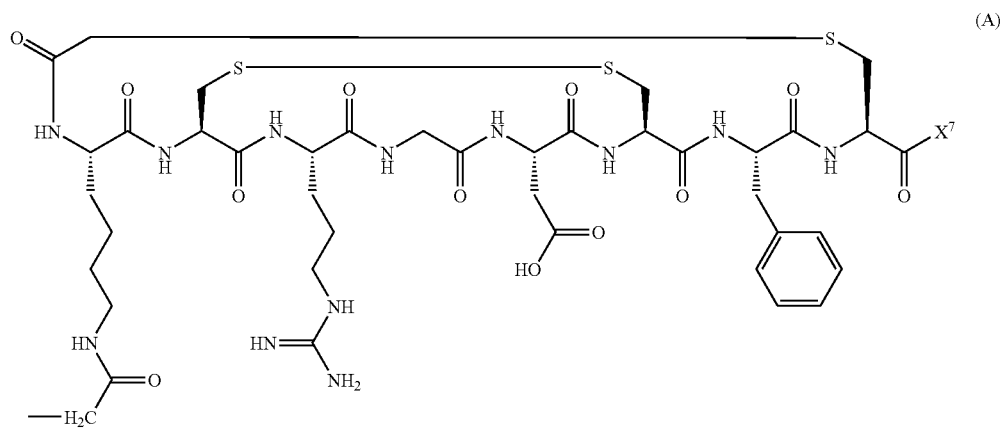

wherein $X^7$ is either —$NH_2$ or

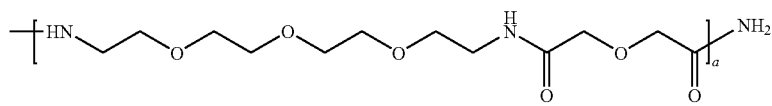

wherein a is an integer of from 1 to 10, preferably a is 1.

As will be appreciated by the skilled person, the methods of the invention may also be used for radiolabelling of other biomolecules such as proteins, hormones, polysaccharides, oligonucleotides, and antibody fragments, cells, bacteria, viruses, as well as small drug-like molecules to provide a variety of diagnostic agents. In formulae (I) and (III) and in other aspects of the invention unless specifically stated otherwise, particularly suitable vectors for radiolabelling are peptides, proteins, hormones, cells, bacteria, viruses, and small drug-like molecules.

The reaction of compound of formula (I) with compound of formula (II) or of compound of formula (III) with compound of formula (IV) may be effected in a suitable solvent, for example acetonitrile, a $C_{1-4}$ alkylalcohol, dimethylformamide, tetrahydrofuran, or dimethylsulphoxide, or aqueous mixtures of any thereof, or in water and at a non-extreme temperature of from 5 to 100° C., preferably at ambient temperature. The Cu(I) catalyst is present in an amount sufficient for the reaction to progress, typically either in a catalytic amount or in excess, such as 0.02 to 1.5 molar equivalents relative to the compound of formula (I) or (III).

Suitable Cu(I) catalysts include Cu(I) salts such as CuI, CuOTf.$C_6H_6$ or [Cu(NCCH$_3$)$_4$][PF$_6$], but advantageously Cu(II) salts such as copper (II) sulphate may be used in the presence of a reducing agent such as ascorbic acid or a salt thereof for example sodium ascorbate, hydroquinone, quinone, metallic copper, glutathione, cysteine, $Fe^{2+}$, or $Co^{2+}$. Cu(I) is also intrinsically presented on the surface of elemental copper particles, thus elemental copper, for example in the form of powder or granules may also be used as catalyst. It has been found that using a Cu(I) catalyst, particularly elemental copper, with controlled particle size, leads to surprisingly improved radiochemical yields. Thus, in one aspect of the invention, the Cu (I) catalyst particularly elemental copper, has a particle size in the range of from 0.001 to 1 mm, preferably of from 0.1 mm to 0.7 mm, more preferably around 0.4 mm.

The present invention provides a more chemoselective approach to radiolabelling where the exact site of introduction of the label is pre-selected during the synthesis of the peptide or vector precursor. The ligation reaction occurring at a pre-determined site in the vector gives only one possible product. This methodology is therefore chemoselective, and its application is considered generic for a wide range of peptides, biomolecules and low-molecular weight drugs. Additionally, the alkyne functionality is stable under most reaction conditions and is unreactive with most common peptide functionalities—thus minimising the protection and deprotection steps required during the labelling synthesis. Furthermore, the isoxazole ring formed during the labelling reaction does not hydrolise and is highly stable to oxidation and reduction, meaning that the labelled vector has high in vivo stability. The isoxazole ring is also comparable to an amide in size and polarity such that the labelled peptides or proteins are good mimics for their natural counterparts.

Compounds of formula (I) and (III) wherein the vector is a peptide or protein may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the alkyne or nitrile oxide group in a compound of formula (I) or (III) may be achieved by reaction of the N or C-terminus of the peptide or with some other functional group contained within the peptide sequence, modification of which does not affect the binding characteristics of the vector. The alkyne groups are preferably introduced to a compound of formula (I) by formation of a stable amide bond, for example formed by reaction of a peptide amine function with an activated acid or alternatively reaction of a peptide acid function with an amine function and introduced either during or following the peptide synthesis. Suitable intermediates useful for incorporation of the alkyne group in a compound of formula (I) include:

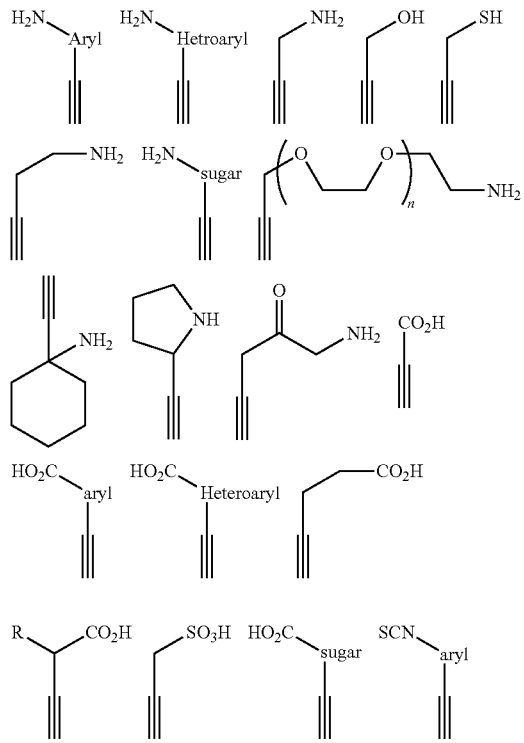

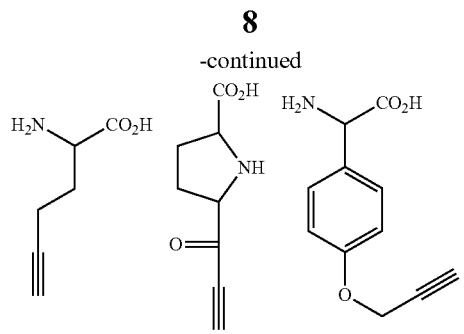

Due to instability of the nitrile oxide group, these are most suitably introduced into a compound of formula (III) in situ, for example from the corresponding aldehyde or masked nitrile oxide, such as a cyclic sulfite ester.

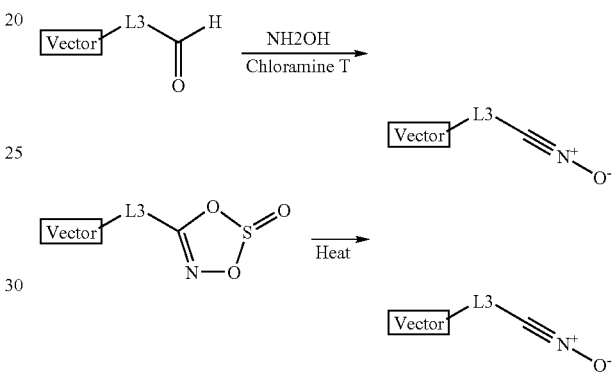

In another aspect, the present invention provides novel prosthetic groups, useful for labelling vectors such as peptides and proteins, for example by the methods described above. Accordingly, there is provided a compound of formula (II):

$$R^*\text{-}L2\text{-}C\!\!=\!\!N^+\!\!-\!\!O^- \qquad (II)$$

wherein L2 is a Linker groups as defined above and R* is a reporter moiety as defined above. In one embodiment of this aspect of the invention, R* is $^{18}F$ such that the prosthetic group is of formula (IIa):

$$^{18}F\text{-}L2\text{-}C\!\!=\!\!N^+\!\!-\!\!O^- \qquad (IIa)$$

wherein L2 is a Linker group as defined above.

In one aspect of the invention, there is provided a compound of formula (II) wherein R* is $^{18}F$ and L2 is phenyl; such compound being readily prepared according to the scheme:

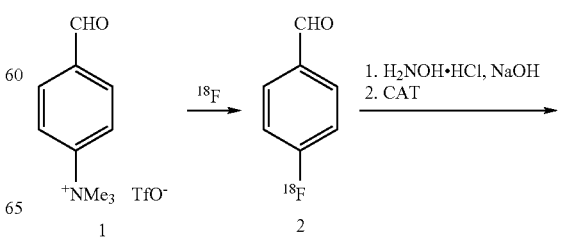

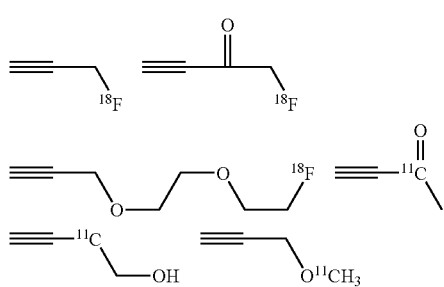

In another aspect, the present invention provides a compound of formula (III):

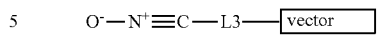

wherein L3 is a Linker group as defined above and the vector is as defined above. Suitably, in this aspect of the invention the vector is a peptide or protein. One group of compounds of formula (III) are those wherein the vector is Arg-Gly-Asp peptide or an analogue thereof such as those described in WO 01/77415 and WO 03/006491, preferably a peptide comprising the fragment

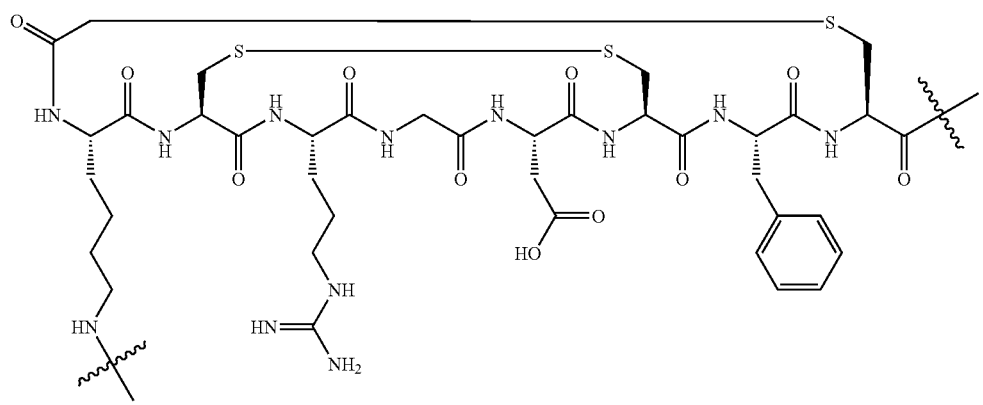

more preferably the peptide of formula (A):

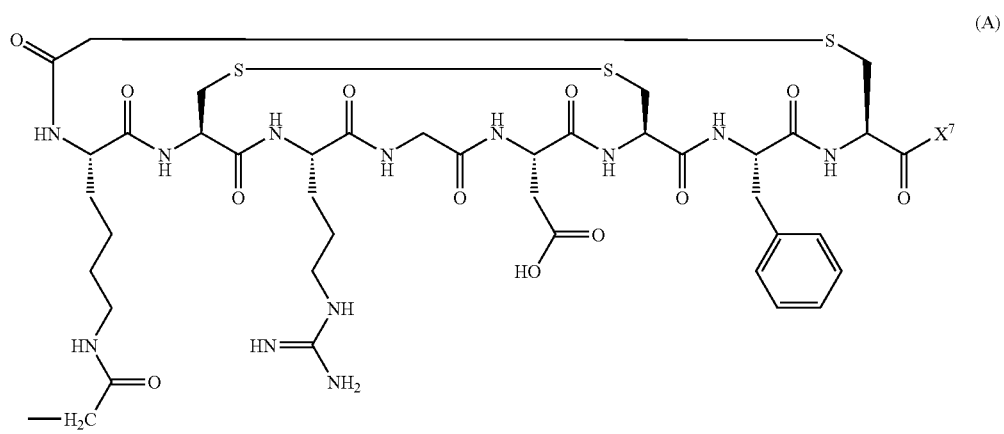

wherein X⁷ is either —NH₂ or

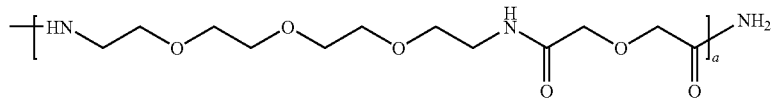

wherein a is an integer of from 1 to 10, preferably a is 1. Such compounds of formula (III) may be useful as precursors for preparation of labelled vectors of formula (VI) as described below.

In a further aspect the present invention provides labelled vectors of formulae (V) and (VI), as defined above. Preferred compounds of formulae (V) and (VI), are those wherein the vector is Arg-Gly-Asp peptide or an analogue thereof, such as those described in WO 01/77415 and WO 03/006491, preferably a peptide comprising the fragment wherein a is an integer of from 1 to 10, preferably a is 1. Such compounds of formula (V) and (VI) may have use for in vivo imaging of a condition associated with cancer, such as angiogenesis.

Compounds of formula (II) wherein R* is ¹⁸F, may be prepared by either electrophilic or nucleophilic [¹⁸F]fluorination of an aldehyde or masked nitrile oxide such as a cyclic sulfite ester, for example:

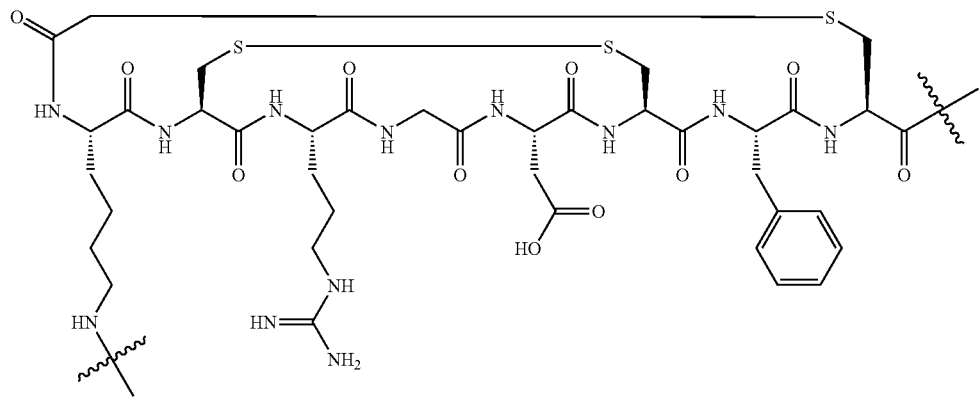

more preferably the peptide of formula (A):

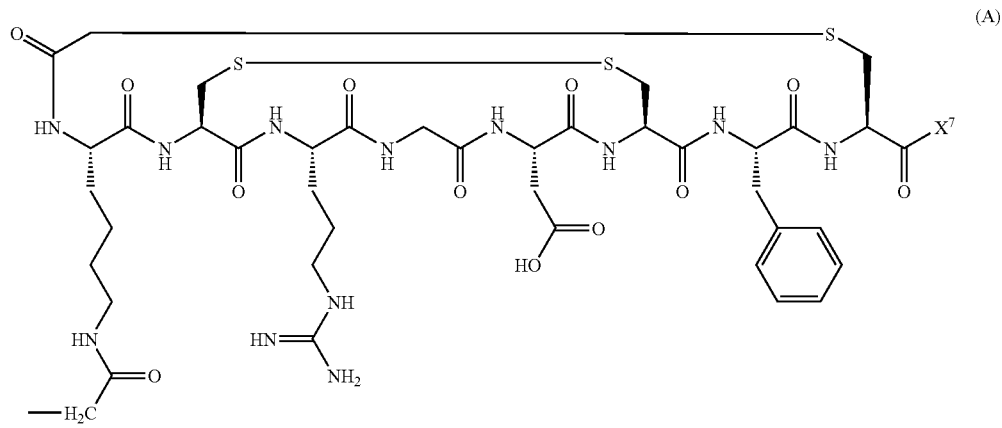

wherein X⁷ is either —NH₂ or

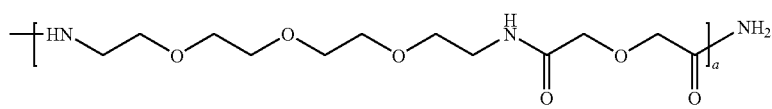

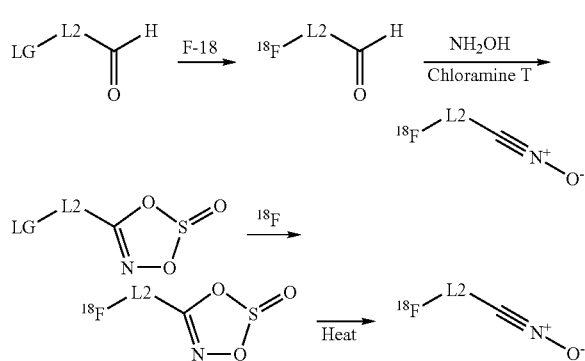

wherein LG is a leaving group as described below and L2 is as defined for the compound of formula (II).

Suitable radiofluorination methods for preparation of a compound of formula (II) include reaction of the aldehyde or masked nitrile oxide precursor incorporating a leaving group (such as an alkyl or aryl sulphonate, for example mesylate, triflate, or tosylate; nitro, or a trialkylammonium salt) with [$^{18}$F]fluoride in the presence of a phase transfer agent such as a cyclic polyether, for example 18-Crown-6 or Kryptofix 2.2.2. This reaction may be performed in solution phase (using an aprotic solvent such as acetonitrile as solvent) under standard conditions known in the art [for example, M. J. Welch and C. S. Redvanly "Handbook of Radiopharmaceuticals", published by Wiley], or using a solid support to facilitate purification of the compound of formula (II) using the methods described in WO 03/002157.

Compounds of formula (IV) may be prepared from suitable acetylene precursors by methods analogous to those described for synthesis of compounds of formula (II).

Compounds of formulae (II) and (IV) wherein R* comprises a chelating agent as described above, either chelated to a metallic radionuclide or suitable for such chelation, may be prepared by methods known in the art, for example as described by Jurisson et al [Chem. Rev., 99, 2205-2218 (1999)], WO 91/01144, and U.S. Pat. No. 4,885,363.

The present invention also provides a radiopharmaceutical composition comprising an effective amount (e.g. an amount effective for use in in vivo imaging, suitably PET or SPECT) of a compound of general formula (V) or (VI) as defined above; together with one or more pharmaceutically acceptable adjuvants, excipients or diluents. Preferably, the vector in the compound of formula (V) or (VI) is Arg-Gly-Asp peptide or an analogue thereof, as described above.

A further embodiment of the invention relates to a compound of general formula (V) or (VI) as defined above, for medical use and particularly for use in in vivo imaging (suitably by PET or SPECT). Preferably, the vector in the compound of formula (V) or (VI) is Arg-Gly-Asp peptide or an analogue thereof, as described above.

The labelled vectors of formulae (V) and (VI) may be administered to patients for in vivo imaging in amounts sufficient to yield the desired signal, typical radionuclide dosages for PET or SPECT imaging of 0.01 to 100 mCi, preferably 0.1 to 50 mCi will normally be sufficient per 70 kg bodyweight.

The labelled vectors of formula (V) or (VI) may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Viewed from a further aspect the invention provides the use of a labelled vector of formula (V) or (VI) for the manufacture of a pharmaceutical for use in a method of in vivo imaging, suitably PET; involving administration of said pharmaceutical to a human or animal body and generation of an image of at least part of said body.

Viewed from a still further aspect the invention provides a method of generating an image of a human or animal body involving administering a pharmaceutical to said body, e.g. into the vascular system and generating an image of at least a part of said body to which said pharmaceutical has distributed using an in vivo imaging technique such as PET, wherein said pharmaceutical comprises a labelled vector of formula (V) or (VI).

Viewed from a further aspect the invention provides a method of monitoring the effect of treatment of a human or animal body with a drug to combat a condition, said method comprising administering to said body a labelled vector of formula (V) or (VI) and detecting the uptake of said labelled vector, said administration and detection optionally but preferably being effected repeatedly, e.g. before, during and after treatment with said drug.

In yet another embodiment of the instant invention, there is provided a kit for the preparation of a radiofluorinated tracer comprising a prosthetic group of formula (II) or (IV) or a precursor thereof and a compound of formula (I) or (III).

In use of the kits, the precursor compound would be converted to the corresponding compound of formula (II) or (IV), using methods described above. The compounds of formula (II) and (IV) may be used in unpurified form, but preferably, the compound of formula (II) and (IV) may be separated from waste reactants by passing the reaction mixture through a Solid Phase Extraction (SPE) cartridge, by chromatography, or by distillation. The compound of formula (II) and (IV) would then be added to the compounds of formula (I) and (III) respectively which may suitably be dissolved in a suitable solvent as described herein. After reaction at a non-extreme temperature for 1 to 90 minutes, the labelled peptide may be purified, for example, by SPE and collected.

The chemistry described herein may also be used to prepare libraries of radiolabelled vectors suitable for screening as diagnostic drugs or in vivo imaging agents. Thus, a mixture of prosthetic groups of formula (II) or (IV) may 30 be reacted with one or more compounds of formula (I) or (III) respectively using the methods described above to yield a library of radiolabelled vectors.

EXAMPLES

The invention is illustrated by way of examples in which the following abbreviations are used:

min.: minute(s)

HPLC: High Performance Liquid Chromatography

DMSO: dimethyl sulfoxide

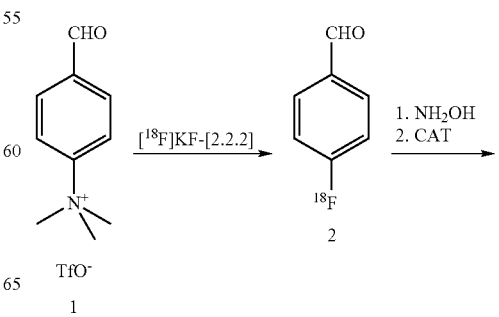

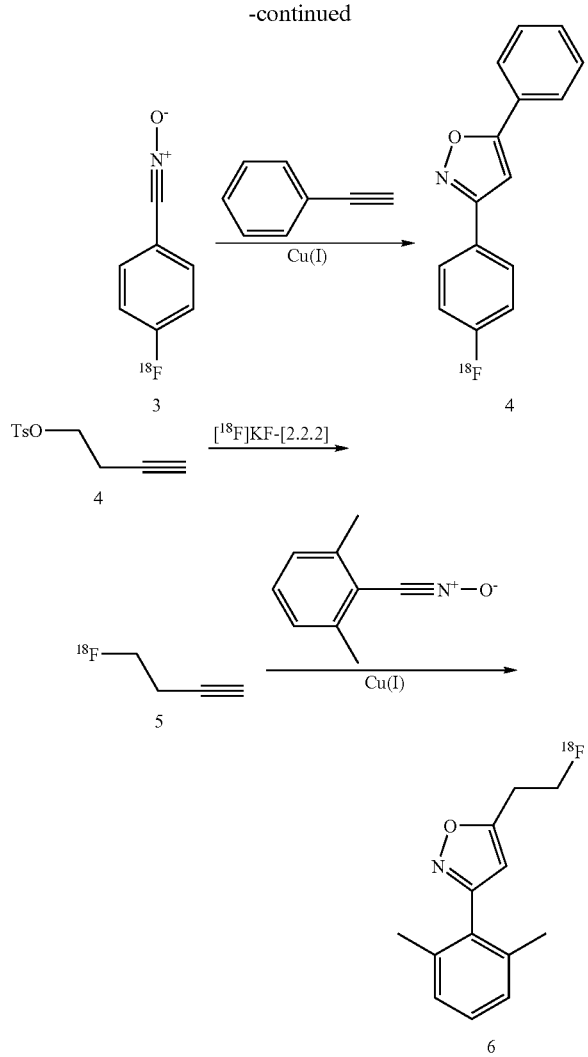

Example 1

Preparation of p-[$^{18}$F]Fluorobenzaldehyde (compound 2)

Fluorine-18 is produced with a cyclotron using the $^{18}$O(p, n)$^{18}$F reaction and 180 enriched water (30%) as target material. Fluorine-18 containing water (370 MBq, 1 mL) is added to a Wheaton vial (2 mL), charged with Kryptofix® 222 (10 mg, 27 μmol), potassium carbonate (1 mg, 7 μmol, dissolved in 0.05 mL water), and acetonitrile (0.8 mL). The solvent is removed by heating at 110° C. for 30 min. under a stream of nitrogen (100 ml/min). Anhydrous acetonitrile (0.5 ml) is added and again evaporated as before. This step is repeated twice. The vial is cooled to room temperature followed by injecting a solution of compound 1 [1 mg, 3.14 μmol, prepared as described by S. M. Haka et al., J. Label. Compds. Radiopharm. 27 (1989) 823] in anhydrous DMSO (0.2 mL). The reaction mixture is stirred at 80° C. for 15 minutes.

Preparation of p-[$^{18}$F]Fluorobenzonitrile N-oxide (compound 3)

To the vial containing compound 2, a solution of hydroxylamine hydrochloride (14.6 mg, 0.21 mmol) in tert-butanol/water (1/1 v/v, 0.1 mL) and sodium hydroxide (8.4 mg, 0.21 mmol) in water (0.1 ml) are added. The mixture is stirred for 30 minutes at room temperature. A solution of Chloramine-T trihydrate (CAT, 59 mg, 0.21 mmol) in water (0.1 mL) is added slowly. The reaction mixture is stirred for 5 minutes at room temperature. Compound 3 is not isolated.

Preparation of [$^{18}$F]3-(4-Fluorophenyl)-5-phenyl-isoxazole (compound 4)

To the reaction mixture containing compound 3, a solution of phenylacetylene (21 mg, 0.21 mmol) in tert-butanol (0.05 mL) and copper powder (5 mg, 0.07 mm particle size) are added. After stirring for 15 minutes at 90° C., compound 4 is isolated by preparative radio HPLC.

Example 2

Preparation of [$^{18}$F]3-Butynylfluoride (compound 5)

Fluorine-18 is produced and modified as Kryptofix® complex as described in Example 1. To this complex, a solution of 3-butynyl p-toluenesulfonate (compound 4, obtained from Aldrich) in anhydrous acetonitrile (0.2 mL) is added. The mixture is heated with stirring for 15 minutes at 80° C. After cooling to room temperature, acetonitrile (0.5 mL) is added. The vial is heated to 100° C. and compound 5 distilled using a stream of nitrogen (10 ml/min) into a trapping vial containing acetonitrile (0.05 mL).

Example 3

Preparation of [$^{18}$F]13-(2,6-Dimethylphenyl)-5-(2-fluoroethyl)-isoxazole (compound 6)

A solution of 2,6-dimethyl benzonitrile N-oxide-[5 mg 0.34 mmol; prepared as described by T. Kubota et al., Chem. Pharm. Bull. 32 (1984) 383] in acetonitrile (0.1 mL) is mixed with an acetonitrile solution (0.05 mL) of compound 5. After adding copper powder (5 mg, 0.07 mm particle size) the vial is heated for 15 minutes at 80° C. Water (0.2 mL) is added, the solution decanted from solid copper, and injected into preparative HPLC for isolating compound 6.

Example 4

Alternative Preparation of Compound 6

An aqueous solution of copper(II) sulfate (0.05 mL, 3.6 mg, 0.0144 mmol) is mixed with sodium ascorbate (0.05 mL, 2.9 mg, 0.0144 mmol) under an nitrogen atmosphere. A solution of 2,6-dimethyl benzonitrile N-oxide (0.2 mg, 0.0144 mmol) in acetonitrile (0.05 mL) is added, followed by compound 5 in acetonitrile (0.05 mL). The reaction mixture is heated for 15 minutes at 80° C. Compound 6 is isolated by quenching water (0.2 mL) and injecting into preparative HPLC.

The invention described and claimed herein is not to be limited in scope by the specific embodiments herein disclosed, since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for labelling a vector comprising reaction of a compound of formula (I) with a compound of formula (II):

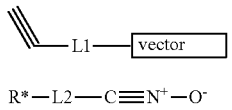

(I)

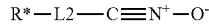

(II)

or,
a compound of formula (III) with a compound of formula (IV)

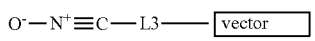

(III)

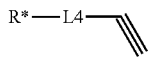

(IV)

in the presence of a Cu (I) catalyst, wherein:
L1, L2, L3, and L4 are each Linker groups;
R* is a reporter moiety which comprises a radionuclide;
to give a conjugate of formula (V) or (VI) respectively:

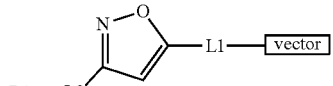

(V)

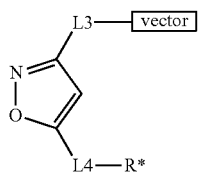

(VI)

wherein L1, L2, L3, L4, and R* are as defined above.

2. A method according to claim 1 wherein R* comprises a positron-emitting radionuclide.

3. A method according to claim 1 wherein the vector is a peptide, protein, hormone, cell, bacterium, virus, or low molecular weight drug.

4. A method according to claim 3 wherein said positron-emitting radionuclide is $^{11}$C or $^{18}$F.

5. A method according to claim 1 wherein the vector is Arg-Gly-Asp peptide.

6. A method according to claim 1 wherein the vector is a peptide comprising the fragment:

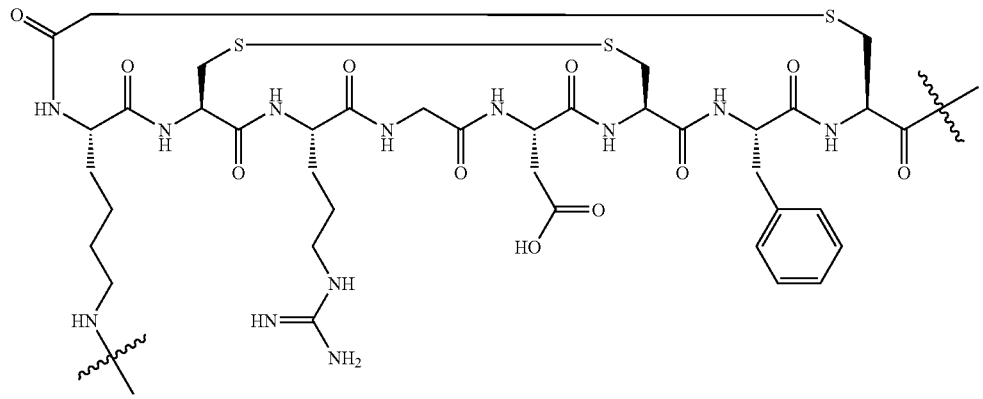

7. A method according to claim 1 wherein the vector is the peptide of formula (A):

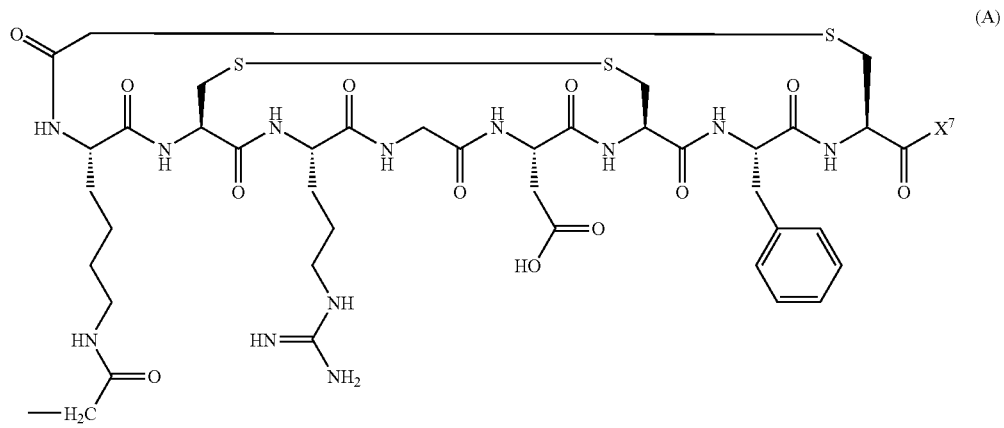

(A)

wherein X[7] is either —NH$_2$ or

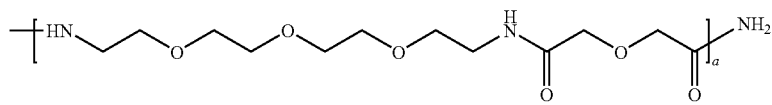

wherein a is an integer of from 1 to 10.

8. A method according to claim 1 wherein elemental copper is used as source of the Cu(I) catalyst.

9. A method according to claim 8 wherein the elemental copper has a particle size in the range of from 0.001 to 1 mm, preferably of from 0.1 mm to 0.7 mm.

10. A method according to claim 9 wherein the elemental copper has a particle size around 0.4 mm.

11. A compound of formula (II):

wherein L2 is a Linker group and R* is a reporter moiety which comprises a radionuclide.

12. A compound according to claim 11 wherein R* is $^{18}$F.

13. A compound of formula (V) or (VI):

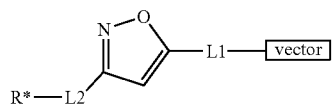

-continued

wherein L1, L2, L3, L4, R* and the vector is a peptide, protein, hormone, cell, bacterium, virus, or low molecular weight drug.

14. A compound of formula (V) or (VI) according to claim 13 wherein the vector is Arg-Gly-Asp peptide.

15. A compound of formula (V) or (VI) according to claim 13 wherein the vector is a peptide comprising the fragment:

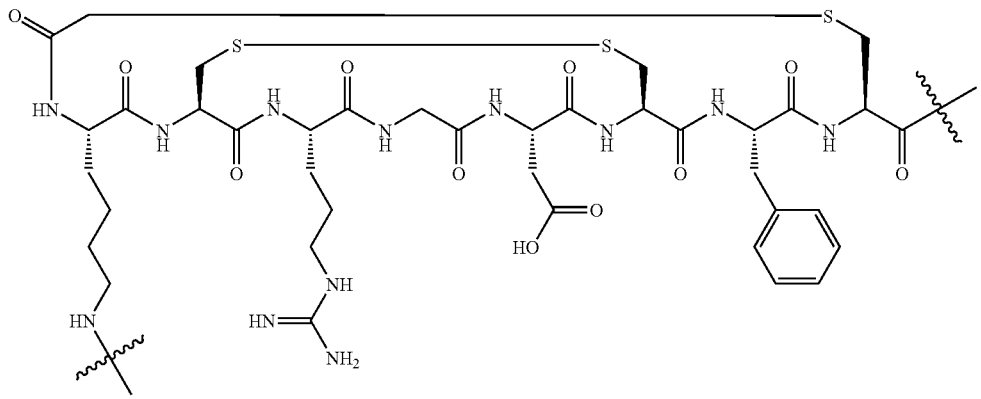

more preferably the peptide of formula (A):

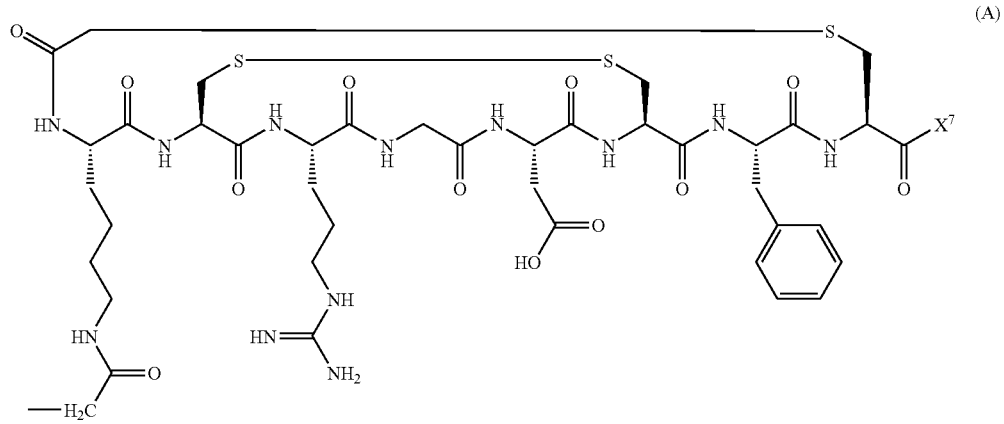

wherein $X^7$ is either —$NH_2$ or

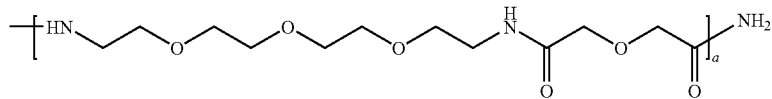

wherein a is an integer of from 1 to 10.

16. A radiopharmaceutical composition comprising an effective amount of a compound according to claim 13; together with one or more pharmaceutically acceptable adjuvants, excipients or diluents.

17. A method of generating an image of a human or animal body comprising administering a compound according to claim 10 to said body and generating an image of at least a part of said body to which said compound has distributed using PET.

18. A compound of formula (III):

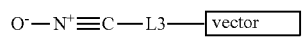

wherein L3 is a Linker groups and the vector is a peptide, protein, hormone, cell, bacterium, virus, or low molecular weight drug.

* * * * *